(12) United States Patent
Torrens Jover et al.

(10) Patent No.: US 7,109,349 B2
(45) Date of Patent: Sep. 19, 2006

(54) PROCESS FOR OBTAINING CIZOLIRTINE AND ITS ENANTIOMERS

(75) Inventors: Antoni Torrens Jover, Barcelona (ES); Helmut H. Buschmann, Barcelona (ES); Stefan Dahmen, Aachen (DE); Matthias Lormann, Aachen (DE)

(73) Assignee: Laboratorios Del Dr. Esteve, S/A, (ES)

( * ) Notice: Subject to any disclaimer, the term of this patent is extended or adjusted under 35 U.S.C. 154(b) by 12 days.

(21) Appl. No.: 11/041,637

(22) Filed: Jan. 24, 2005

(65) Prior Publication Data

US 2006/0135788 A1   Jun. 22, 2006

(30) Foreign Application Priority Data

Dec. 7, 2004   (EP)   .................. 04380266

(51) Int. Cl.
*C07D 231/12*   (2006.01)
(52) U.S. Cl. .................................. 548/375.1
(58) Field of Classification Search ............. 548/375.1
See application file for complete search history.

(56) References Cited

U.S. PATENT DOCUMENTS 6,118,009 A * 9/2000 Torrens-Jover et al. .. 548/375.1

FOREIGN PATENT DOCUMENTS

| EP | 0 289 380 B1 | 12/1994 |
| EP | 1 029 852 B1 | 11/2002 |
| WO | WO 99/02500 | 1/1999 |
| WO | WO 99/07684 | 12/1999 |

OTHER PUBLICATIONS

Bolm, Carsten, et al., Synthesis of Novel 1,1'-Bis(oxazolinyl)metallocenes and their Application in the Asymmertic Phenyl Transfer from Organozincs to Aldehydes, *Journal of Organometallic Chemistry* vol. 624, (2001) 157-161.
Bolm, Carsten, et al., Polymer-Supported Ferrocenyl Oxazolines for the Catalyzed Highly Enantioselective Phenyl Transfer to Aldehydes, *Bioorganic & Medicinal Chemistry Letters* vol. 12, (2002) 1795-1798.
Bolm, Carsten, et al., Catalyzed Asymmetric Aryl Transfer Reactions to Aldehydes with Boronic Acids as Aryl Source, *J. Am. Chem. Soc.* vol. 124, (2002) 14850-14851.
Dosa, Peter I., et al., Planar-Chiral Heterocycles as Ligands in Metal-Catalyzed Processes: Enantioselective Addition of Organozinc Reagents to Aldehydes, *J. Org. Chem.* vol. 62, (1997) 444-445.
Fontes, Montserrat, et al., 2-Piperidino-1,1,2-Triphenylethanol: A Highly Effective Catalyst for the Enantioselective Arylation of Aldehydes, *J. Org. Chem.* vol. 69, (2004) 2532-2543.
Huang, Wei-Sheng, et al., New and Improved Ligands for Highly Enantioselective Catalytic Diphenylzinc Additions to Aryl Aldehydes, *Tetrahedron Letters* vol. 41, (2000) 145-149.
Hueso-Rodriguez, Juan A., et al., Preparation of the Enantiomers of the Analgesic E-3710, *Bioorganic & Medicinal Chemistry Letters*, vol. 3, (1993) 269-272.
Noyori, Ryoji, et al., Asymmetric Catalysis by Architectural and Functional Molecular Engineering: Practical Chemo-and Stereoselective Hydrogenation of Ketones, *Angew. Chem. Int. Ed.*, vol. 40, (2001) 40-73.
Pu, Lin, et al., Catalytic Asymmetric Organozinc Additions to Carbonyl Compounds, *Chem. Rev.* vol. 101, (2001) 757-824.
Rudolph, Jens, et al., Highly Enantioselective Synthesis of Secondary Alcohols Using Triphenylborane, *Adv. Synth. Catal.* vol. 346, (2004) 867-872.
Shibata, Takanori, et al., Highly Enantioselective Catalytic Asymmetric Automultiplication of Chiral Pyrimidyl Alcohol, *J. Am. Chem. Soc.* vol. 118, (1996) 471-472.
Smith, Thomas E., et al., Effects of Base, Electrophile, and Substrate on the Selective Alkylation of Heteroaromatic Systems, *Heterocycles*, vol. 57, (2002) 1211-1217.
Torrens, Antoni, et al., Optical Resolution and Enantiomeric Purity Determination of the Analgesic Cizolirtine, *Chirality*, vol. 11, (1999) 63-69.

* cited by examiner

*Primary Examiner*—Kamal A. Saeed
(74) *Attorney, Agent, or Firm*—Steven J. Hultquist; Intellectual Property Technology Law

(57) ABSTRACT

A process is described for the preparation of a precursor alcohol of Cizolirtine, (±)-2-[phenyl(1-methyl-1H-pyrazol-5-yl)methoxy]-N,N-dimethylethanamine and its enantiomers. The process involves the asymmetric addition of a metalated phenyl reagent to a pyrazolcarbaldehyde in the presence of a chiral ligand to yield chiral alcohols. The chiral alcohols are further O-alkylated to yield Cizolirtine or its enantiomers.

18 Claims, No Drawings

PROCESS FOR OBTAINING CIZOLIRTINE AND ITS ENANTIOMERS

CROSS-REFERENCE TO RELATED APPLICATION

The priority of European Patent Application EP04380266.9 filed Dec. 17, 2004 is hereby claimed under the provisions of 35 USC §119.

FIELD OF THE INVENTION

The present invention relates to the asymmetric addition of a metalated phenyl reagent to a heteroaryl aldehyde to render chiral alcohols. More particularly, it relates to a new process for the preparation of the pure enantiomers of an intermediate alcohol which is used in the preparation of Cizolirtine, (±)-2-[phenyl(1-methyl-1H-pyrazol-5-yl)methoxy]-N,N-dimethylethanamine and its enantiomers, including the enantioselective addition reaction of a phenyl zinc reagent to a pyrazolcarbaldehyde.

BACKGROUND OF THE INVENTION

The compound (±)-2-[phenyl(1-methyl-1H-pyrazol-5-yl)methoxy]-N,N-dimethylethanamine, also referred to as (±)-5-[α-(2-dimethylaminoethoxy)benzyl]-1-methyl-1H-pyrazole, or Cizolirtine, of formula (I)

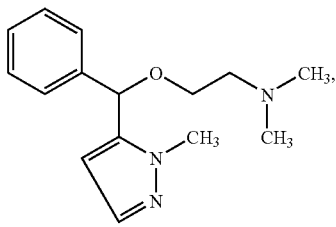

(I)

is described in the European Patent EP 289 380. This compound is a potent analgesic which is currently in phase II clinical trials.

The two enantiomers of Cizolirtine, hereinafter referred to as (+)-I and (−)-I, have been previously obtained by optical resolution of the Cizolirtine racemate by fractional crystallization with optically active acids (as described in International Patent Publication WO 99/02500) such as, for instance, with (−)- and (+)-di-p-toluoyltartaric acid (Torrens, A.; Castrillo, J. A.; Frigola, J.; Salgado, L.; Redondo, *J. Chirality*, 1999, 11, 63). The study of their analgesic activities has shown that the dextrorotatory enantiomer, (+)-I, is more potent than the (−)-I. An enantiomerically pure compound synthesis (EPC synthesis) starting from ethyl (R)-mandelate of the intermediate permitted the assignment of the (R) absolute configuration to the (+)-I isomer (Hueso-Rodriguez, J. A.; Berrocal, J.; Gutiérrez, B.; Farré, A.; Frigola, *J. Bioorg. Med. Chem. Lett.* 1993, 3, 269).

The (±)-Cizolirtine has been prepared by O-alkylation of compound (±)-II of formula II:

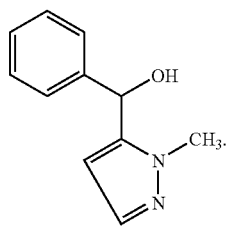

(II)

The pure enantiomers of Cizolirtine (+)-I and (−)-I may be prepared by separately O-alkylating the enantiomerically pure intermediates (+)-II and (−)-II.

The enantiomerically pure compounds (+)-II and (−)-II are obtained either by reduction of a compound of formula III, which yields (±)-II as a racemate, followed by procedures of optical resolution of the racemate (±)-II, such as by fractional recrystallization from solvents or column chromatography [J. A: Hueso, J. Berrocal, B. Gutiérrez, A. J. Farré y J. Frigola, *Bioorg. Med. Chem. Lett.* 1993, 3, 269], or by EPC synthesis starting from the prochiral ketone of formula III:

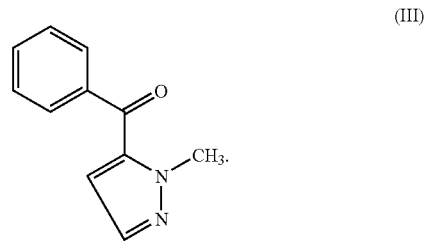

(III)

The enantioselective reduction of prochiral ketones in organic synthesis to obtain secondary alcohols with high enantiomeric purity is of high interest since they can be valuable intermediates for the manufacture of active compounds. Accordingly, a number of strategies for the asymmetric reduction of prochiral ketones to single enantiomer alcohols have been developed [R. Noyori, T. Ohkuma, *Angew. Chem. Int. Ed.*, 2001, 40, 40–73, Wiley-VCH Verlag]. Particularly, the use of oxazoborolidines as ligands or catalysts constitutes a major advance in the asymmetric reduction of prochiral ketones. The use of such chiral ligands or catalysts in combination with achiral reducing agents for the preparation of (+)-I and (−)-I has been described in European Patent EP 1 029 852 B1. However, for diaryl methanols, the reduction of the corresponding ketone precursors is problematic. The chiral catalyst has to differentiate between the two aromatic rings. This can usually only be done with high selectivity if the two rings are different in terms of steric and/or electronic properties, which is not obvious in the case of Cizolirtine.

Another strategy for the enantioselective reduction of prochiral ketones with high enantiomeric excess involves the use of a diphosphane/Ru/chiral diamine/inorganic base catalyst system. However, this process leads to the formation of heavy metal complexes of Ru or elemental Ru and trace amounts of such metal are very hard to remove.

A phenyl transfer reaction to aryl aldehydes as an approach towards enantio-pure diarylalcohols has also been proposed, as an alternative to the enantioselective reduction of prochiral ketones [P. I. Dosa, J. C. Ruble, G. C. Fu, *J. Org. Chem.* 1997, 62 444; W. S. Huang, L. Pu, *Tetrahedron Lett.* 2000, 41, 145; M. Fontes, X. Verdaguer, L. Solá, M. A. Pericás, A. Riera, *J. Org. Chem.* 2004, 69, 2532]. For this transformation, the group of Bolm et al. developed a protocol which utilized a ferrocene-based ligand (or catalyst) and diphenylzinc in combination with diethylzinc as an aryl source [C. Bolm, N. Hermanns, M. Kesselgruber, J. P. Hildebrand, *J. Organomet. Chem.* 2001, 624, 157; C. Bolm, N. Hermanns, A. Classen, K. Muñiz, *Bioorg. Med. Chem. Lett.* 2002, 12, 1795]. Enantiomerically enriched diarylmethanols with excellent enantiomeric excess (up to 99% ee) were thus obtained in a straightforward manner. Subsequently, the applicability of air-stable arylboronic acids as an aryl source was also demonstrated [C. Bolm, J. Rudolph, *J. Am. Chem. Soc.* 2002, 124, 14850]. However, these systems require a high catalyst loading (of commonly 10% mol.) to achieve such high enantioselectivity. With the aim of reducing this problem, recently, the use of triphenylborane has been proposed as an alternative phenyl source in a reaction where the ferrocene-based catalyst is also used (J. Rudolph, F. Schmidt, C. Bolm, *Adv. Synth. Catal.* 2004, 346, 867).

However, there are still some difficulties to obtain chiral alcohols with a high yield and enantioselectivity without a high amount of catalyst. For their large-scale preparation, the application of highly efficient catalytic systems and enantioselective methods employing inexpensive starting materials and simple purification steps would be most desirable.

On the other hand, there is at the present time no example of an enantioselective addition of phenyl- or arylzinc reagents to heteroaryl aldehydes which comprise one or two nitrogen atoms, such as methyl-pyrazol aldehyde. This is understandable, since substrates containing a nitrogen heteroatom can be expected to form catalytically active complexes (or product complexes), which would usually drastically diminish the selectivity by favouring competing catalytic pathways. Indeed, it is well known in zinc chemistry that various functional groups like esters or nitrites are tolerated on the aldehyde substrates. However, Lewis-basic or coordinating functional groups often lead to drastic decreases in enantioselectivity in arylzinc addition reaction, due to their ability to complex to the zinc reagent or the active catalyst. An extreme example of this behaviour would be the asymmetric autocatalysis in the addition of zinc reagents to aldehydes as examined by Soai et al. (T. Shibata, H. Morioka, T. Hayase, K. Choji, K. Soai *J. Am. Chem. Soc.* 1996, 471).

Thus, to attain satisfactory ee values by an enantioselective addition reaction, an appropriate coordination of the catalyst system and the aldehyde is required. The results with unusual substrates cannot be predicted, and each addition has to be investigated separately with regard to the substrate.

SUMMARY OF THE INVENTION

We have now surprisingly found that pyrazolcarbaldehydes can be successfully used as substrates for a phenyl transfer reaction. Indeed, the reaction works remarkably well even in the presence of two N on the heteroaromatic part of the aldehyde, providing the desired diarylmethanols with high conversion and high enantiomeric purity. We have therefore applied this process to the synthesis of the enantiomerically pure intermediates (+)-II and (−)-II and to a process to obtain Cizolirtine and its enantiomers. This process is contemplated to operate particularly well on an industrial scale, and in a satisfactory manner with regard to enantiomer excess, amount and availability of catalyst, and raw material costs generally. Further, heavy metals are not used, thereby avoiding the presence of potentially toxic impurities, and impurities are easily eliminated.

Accordingly, in one aspect the present invention refers to a process for asymmetric addition to a pyrazolcarbaldehyde with a phenyl zinc reagent in the presence of a chiral ligand. Such process allows the preparation of known intermediates of formula (II), which thereafter can yield, by O-alkylation, the desired enantiomers of the pharmaceutically active compound Cizolirtine.

The invention thus is directed to a process for the preparation of an enantiomerically enriched compound of formula (II):

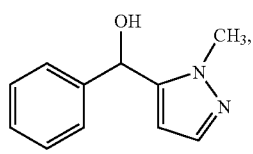

which includes an enantioselective addition reaction to a pyrazolcarbaldehyde compound of formula (IV):

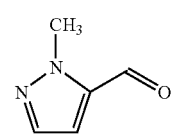

with a phenyl zinc reagent in the presence of a chiral ligand.

Other aspects, features and advantages of the invention will be more fully apparent from the ensuing disclosure and appended claims.

DETAILED DESCRIPTION OF THE INVENTION

The process of the invention gives the desired product of formula II with high conversion and enantiomeric excess. This process has the further advantage that the zinc salts used or formed during the reaction are easily removed by aqueous work-up. The product of formula II is especially useful in the preparation of Cizolirtine enantiomers. The details of the process are discussed below.

Pyrazolcarbaldehyde

The synthesis of 2-methyl-2H-pyrazole-3-carbaldehyde (IV), which is the essential starting material for the addition route, is known to the person skilled in the art. For example, (IV) can be easily prepared through the lithiation of 1-methyl pyrazol and concomitant quenching with dimethyl formamide (DMF). The reaction product then is hydrolyzed, for example with water or sodium acetate buffer (pH 4.5), and either employed directly or after distillation (scheme I). Residual amounts of DMF do not appear to influence the selectivity of the subsequent addition process.

Scheme I

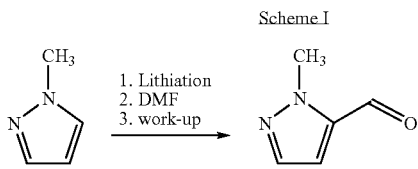

Optimal conditions for the lithiation are found in the literature (T. E. Smith, M. S. Mourad, A. J. Velander, *Heterocycles* 2002, 57, 1211) and can be employed in the formylation reaction. If necessary, diethyl amine can be used to prevent the deprotonation of the N-methyl group, and normally 10 mol % is sufficient. Preferably, THF is used as a solvent; in this case no additive is necessary. The deprotonation reaction is preferably performed below −10° C. (usually at −20° C.) to prevent the formation of side products by ring-opening of THF. To purify the obtained 1-methylpyrazolcarbaldehyde, distillation or extractive workup with an organic solvent can be used to remove the by-products. Otherwise, as previously mentioned, the aldehyde can be used directly for the addition.

Phenyl Zinc Reagent

The phenyl zinc reagent to be used in the process of the invention is also known to the person skilled in the art, as mentioned above. For example, it can be diphenylzinc or a mixed zinc species generated from diphenylzinc and diethylzinc or it can be prepared in situ by a transmetallation reaction of a phenylboron reagent with dimethyl- or diethylzinc. The active species are presumably a mixed phenyl-ethyl-zinc or phenyl-methyl-zinc. Among the suitable phenyl-boron reagents, phenylboronic acid (C. Bolm, J. Rudolph *J. Am. Chem. Soc.* 2002, 124, 14850), triphenylborane (J. Rudolph, F. Schmidt, C. Bolm, *Adv. Synth. Catal.* 2004, 346, 867), triphenylborane ammonia complex or 2-aminoethyl diphenylborinate can be used.

Diphenylzinc and triphenylborane are relatively expensive reagents. Therefore, stable complexes of aryl boranes are preferred. Triphenylborane ammonia complex, which can readily be prepared from commercially available triphenylborane sodium hydroxide complex, has proven very suitable. Additionally, commercially available and stable 2-aminoethyl diphenylborinate can be employed. Preferably, the phenyl-boron reagent is triphenylborane ammonia complex.

A variable that can affect the enantioselectivity of the addition reaction is the ratio of borane reagent versus diethylzinc (when the phenyl zinc reagent is obtained from these compounds). For example, when using triphenylborane as a borane reagent, it could appear obvious that this ratio must be 1:3 since each borane contains 3 phenyl groups which are theoretically transferable to the aldehyde. However, for this system the optimal value has been determined to be two phenyl groups (equalling ⅔ equivalents of triphenylborane) per one equivalent of diethylzinc.

Chiral Ligand

With the aim of enantioselectively synthesizing a compound of formula (II) by an addition reaction, the reaction must be carried out in the presence of a chiral catalyst or ligand, which forms the active catalyst in situ by reaction with the zinc reagent. That means that the ligand (or catalyst) must have at least one element of chirality, such as one or more stereocenters or elements of planar chirality.

In principle, there is a great variety of N,O—, N,N—, N,S—, N,Se— or O,O-ligands that can be used in the process of the invention and all of them have to be in enantiomerically pure form. There are about 600 ligands known in the art for this type of reaction. Most of them can be found, for example, in a recent review on catalytic asymmetric organozinc additions to carbonyl compounds [L. Pu, H.-B. Yu, Chem. Rev. 2001, 101, 757]. The nomenclature N,O—, N,N—, N,S—, N,Se— or O,O— refers to ligands that have at least these two coordinating heteroatoms.

In a preferred embodiment of the present invention N,O-ligands are employed. In general they are derived from β-amino alcohols and therefore have two carbon atoms between the heteroatoms. However, some of the ligands that can be usefully employed in this reaction are those which present three carbon atoms between the heteroatoms.

These ligands react with the zinc reagent forming a zinc-alcoxide complex which is more Lewis-acidic than the other present zinc species (reagent and product). Additionally, it is a Lewis-base catalyst (usually at the oxygen atom). This zinc-alcoxide complex formed in situ is the active catalyst.

More preferably, the O is an alcohol. In this case, preferred ligands have a structure-type (V) such as described below:

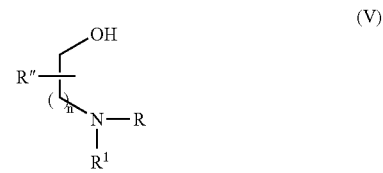

wherein n is 0 or 1.

Typical ligands useful in this addition reaction include the following compounds, their enantiomers, and derivatives thereof:

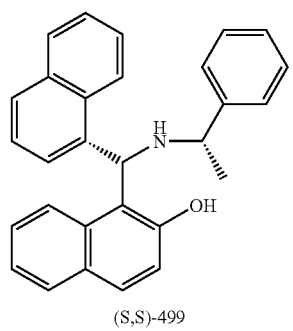

(S,S)-499

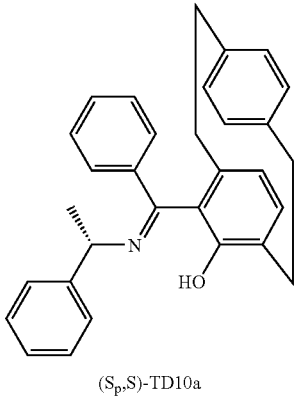

(S$_p$,S)-TD10a

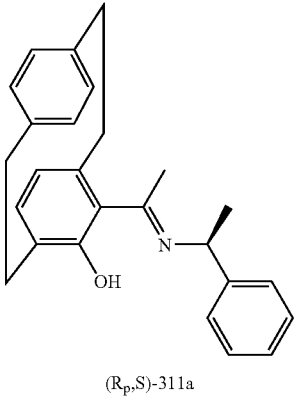

(R$_p$,S)-311a

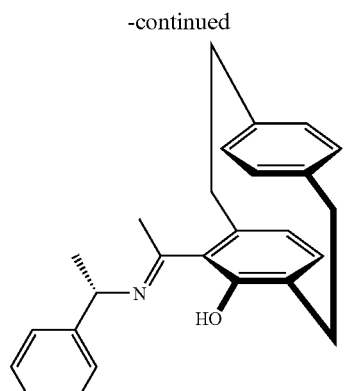

SD-311b

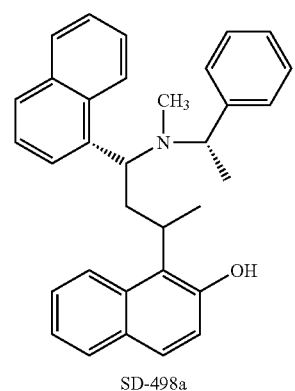

SD-498a

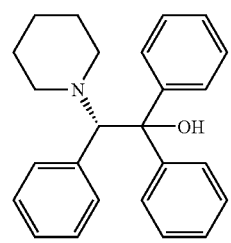

(S)-2-piperidinyl-1,1,2-triphenylethanol

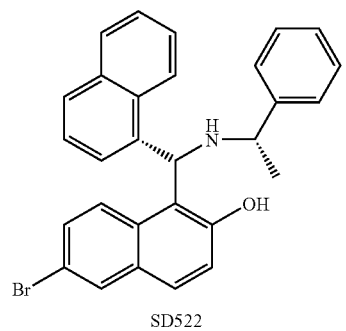

SD522

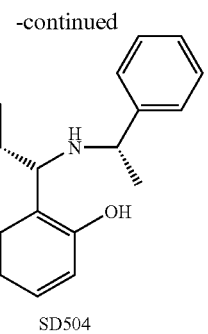

SD504

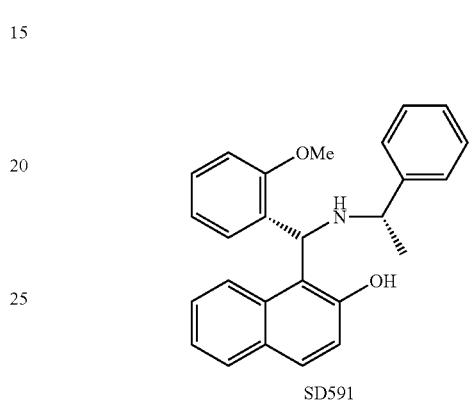

SD591

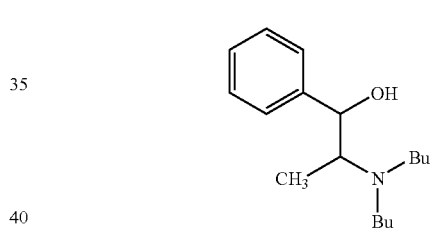

(1R, 2S)-(-)-2-dibuthylamine-1-phenyl-propanol

By way of example, good results have been obtained with sd311b and with commercially available (S)-2-piperidinyl-1,1,2-triphenylethanol:

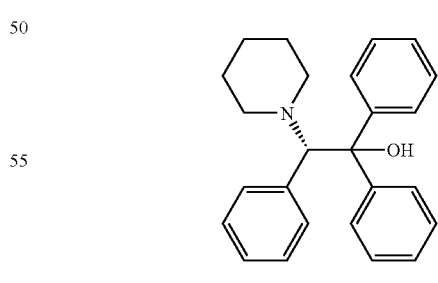

In an illustrative synthesis, 96.5% of the R-enantiomer alcohol versus 3.5% of the S was obtained using 10 mol % of this ligand. The ligand is available in both enantiomeric forms, allowing the synthesis of both enantiomers of the desired alcohol.

The reaction that takes place between the zinc reagent and the ligand leads to a complex of formula (VI):

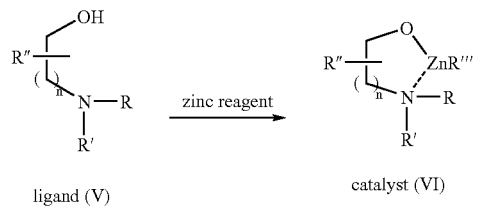

ligand (V)    catalyst (VI)

wherein n is 0 or 1 and R''' is phenyl, ethyl or methyl.

This zinc alkoxide complex (VI) is the active catalyst in the addition reaction, which subsequently coordinates with the pyrazolcarbaldehyde in such a way as to induce the enantioselective addition of the phenyl group to the aldehyde.

The concentration of the ligand should be low to reduce costs, but sufficient to provide good ee. The ligands preferably are used in amounts of 0.1 to 100 mol %, more preferably 1 to 20 mol % and most preferably 5 to 10 mol %. The use of more than the optimal amount of ligand is uneconomical and in some cases can lead to lower selectivity. On the contrary, using less than optimal amount of ligand diminishes the selectivity due to a stronger influence of the non-catalyzed and non-enantioselective background reaction.

Solvent

Suitable solvents for the process of the invention are known from similar reactions and can be found in the above-mentioned references. Preferred solvents include non-coordinating hydrocarbons such as pentane, hexane, heptane; aromatic solvents such as benzene and toluene; chlorinated solvents such as dichloromethane and 1,2-dichloroethane, and weakly coordinating solvents such as diethyl ether and methyl-tert-butyl ether (MTBE). The most preferred solvents are toluene and hexane. These solvents allow the optional O-alkylation to be carried out in the same reaction mixture.

To perform the process, a mixture of ligand and the compounds that form the zinc reagent can be prepared and stirred, before the addition of the aldehyde. Usually, a pre-stirring is presumed to be beneficial for the selectivity, because the deprotonation of the ligand by the zinc reagent to yield the active catalyst requires a certain amount of time.

Unexpectedly, it has been found that higher enantiomeric excess is achieved if short pre-stirring times are used. The highest selectivity was obtained upon simultaneous addition of aldehyde and diethylzinc. Thus, in a preferred embodiment these reagents are simultaneously added. Once the aldehyde is added to the mixture of ligand and zinc reagent, the reaction time ranges between 1 hour and 24 hours.

The concentration of the aldehyde in the reaction is preferably low, e.g., in a range of from 0.01 molar to 2 molar, more preferably in a range of from 0.1 to 1 molar, and most preferably at a concentration of about 0.1 molar. Although in some cases it has been seen that enantioselectivity increases at lower concentrations, this is not suitable for an industrial process. In these cases a proper balance between enantioselectivity and adequate concentrations has to be found.

The process of the invention can be carried out at temperature in a range of from −40 to 100° C. Preferably, temperatures between 0 and 20° C. are used. Most preferably, the reactions are carried out at temperature in the vicinity of 10° C. The person skilled in the art can readily determine without undue experimentation the optimal temperature for each combination of reagents. The enantioselectivity of the reaction can also be dependent on the reaction temperature.

The process of the invention can also comprise the presence of additives, for example in order to improve the enantioselectivity by scavenging or complexing Lewis-acidic zinc salts present in the reaction or formed as products.

Suitable additives are for example alcohols, amines or derivatives of polyethyleneglycol. More preferably the additive is selected from polyethyleneglycols such as DiMPEG 1000, DiMPEG 2000, PEG 750, PEG 1000, PEG 2000, monoMPEG 2000 and PE-block-PEG, or from compounds such as 1,4-dioxane, i-propanol and triethylamine.

In one preferred embodiment, the process is directed to the synthesis of each of the following alcohols of formula II with the highest possible enantiomeric purity:

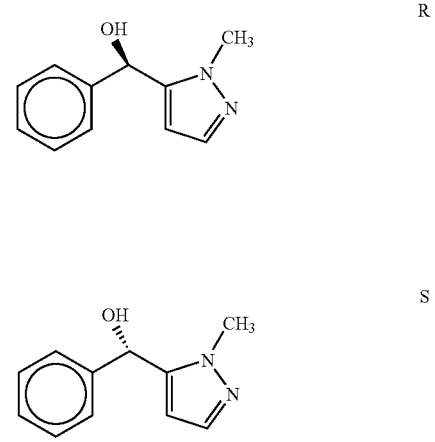

The obtained alcohol can be purified through chromatography or crystallization; the zinc salts used or formed during the reaction are easily removed by aqueous work-up.

Alternatively, the alcohol can advantageously be used without further purification in the next step, which can be carried out in the same reaction medium.

Thus, in another aspect, the invention relates to a process as defined above which further includes the step of O-alkylation of an enantiomerically enriched compound of formula (II) to yield the desired enantiomer of the pharmaceutically active Cizolirtine (I). To this end, the compound of formula (II) is treated with an amine of the formula $$X-CH_2CH_2N(Me)_2,$$

wherein X is a suitable leaving group such as halogen, more preferably chlorine, bromine or iodine; a reactive esterified hydroxyl, for example arylsulfonyloxy such as phenylsulfonyloxy; tosyloxy; mesyloxy; $C_{1-4}$ alkyl sulfonyloxy, for example methanesulfonyloxy; arylphosphoryloxy, for example diphenylphosphoryloxy, dibenzylphosphoryloxy or a $C_{1-4}$ alkyl phosphoryloxy, for example dimethylphosphoryloxy.

An appropriate O-alkylation has been described in European Patent EP289 380 or International Patent Publication WO 99/07684, the disclosures of which hereby are incorporated herein in their entirety.

The alkylation preferably is carried out directly in the same reaction medium resulting from the process of the invention, without further purification of the carbinol. In general, the O-alkylation is carried out in conditions of phase transfer, using for example 2-chloro-N,N,-dimethyl-ethylamine (other leaving groups instead of chloro are possible), an alkaline aqueous solution such as NaOH or KOH, in the presence of a catalyst such as a quaternary ammonium salt. Accordingly, the same solvent as the one used in the process of the invention is used, such as toluene. In these conditions we have the further advantage that impurities such as any remaining zinc salts are also eliminated through the aqueous phase.

The resulting product of formula I is enantiomerically enriched, and it can be further purified using polar organic solvents. Further, a pharmaceutically acceptable salt of the compound of formula I can be formed. For example, the citrate salt can be prepared by dissolving the amine of formula I in ethanol and treating the solution with citric acid monohydrate. The preparation of other salts will be readily apparent to the person skilled in the art.

The following examples will further illustrate the invention, and are not to be interpreted as limiting, as regards the scope of the invention.

EXAMPLES

Example 1

Synthesis of 2-Methyl-2H-pyrazole-3-carbaldehyde

In a dry 50 ml vial is placed a solution of 1.642 g (20 mmol) N-methylpyrazole in 30 ml dry THF. The mixture is cooled to −20° C. and while stirring 8 ml (20 mmol, 2.5M in hexane) n-BuLi-solution is slowly added. The reaction mixture is stirred for 2.5 hours at −20° C. With vigorous stirring 4.7 ml (4.39 g, 60 mmol) dry DMF is slowly added at −20° C. and the mixture kept at this temperature for 1 hour. The reaction mixture then is poured into 100 ml of a 1 M acetic acid/sodium acetate buffer (pH 4.5), 50 ml MTBE is added and the organic layer is separated, washed with 50 ml saturated $Na_2CO_3$-solution to remove excess acetic acid (extraction with ethyl acetate leads to DMF in the final product). The organic layer is separated, dried with $MgSO_4$ and the solvent is removed using a rotary evaporator. The crude product is purified by vacuum distillation (bp: 67° C., 21 mbar). Three preparations which were distilled together yielded 5.969 g (54 mmol, 90%) of the title compound.

$^1$H-NMR (300 MHz, $CDCl_3$): 4.18 (s, 3H, $CH_3$—N), 6.91 (d, 1H, $^3J$=2.0 Hz, CH=C—N), 7.53 (d, 1H, $^3J$=2.0 Hz, CH=N), 9.87 (s, 1H, CH=O) ppm.

$^{13}$C-NMR (100 MHz, $CDCl_3$): 39.31 ($CH_3$—N), 114.78 (CH=C—N), 138.54 (CH=N), 138.98 (CH=C—N), 179.83 (CH=O) ppm.

Example 2

Synthesis of (2-Methyl-2H-pyrazol-3-yl)-phenyl-methanol using triphenylborane ammonia complex In a 20 ml vial is placed 8.91 mg (10 mol %) of (S)-2-piperidinyl-1,1,2-triphenyl-ethanol and 43 mg (0.17 mmol) of triphenylborane ammonia complex. The vial is closed and flushed with argon. Dry toluene (2 mL) is added and the vial is placed in a cooling bath of 10° C. Diethylzinc (0.7 mL, 15% in hexane) and 25 µl (0.25 mmol) 2-methyl-2H-pyrazole-3-carbaldehyde is added and the reaction mixture is stirred for at least 12 hours at 10° C. The reaction is quenched by addition of 2 mL of 1 M HCl with vigorous stirring. The reaction mixture is placed in a separation funnel, 10 ml 1M HCl and approximately 25 mL MTBE is added. The organic layer is washed with 15 mL of saturated $Na_2CO_3$-solution, dried with $MgSO_4$ and the solvent is removed by a rotary evaporator to yield 40 mg of the crude product. The product can be further purified by column chromatography on silica using ethyl acetate/hexane (1:1) as eluent to yield (R)-II (37 mg, 79%) in 93% ee.

Evaluation of enantiomeric excess:

HPLC Column: Diacel Chiralcel OD 250×4 mm heptane/propane-2-ol 80/20

Flow: 1 ml/min; Temperature: 20° C.; det.: 220 nm

Ret-Times: 8.5 min (R-Enantiomer)/9.6 min (S-Enantiomer)

$^1$H-NMR (400 MHz, $CDCl_3$): 3.73 (s, 3H, $CH_3$—N), 5.87 (s, 1H, CH—OH), 6.02 (dd, 1H, $3J$=1.98, $4J$=0.49 Hz, CH=C—N), 7.30 (d, 1H, $3J$=1.98 Hz, CH=N), 7.30–7.38 (m, 5H, $CH_{arom}$) ppm.

$^{13}$C-NMR (100 MHz, $CDCl_3$): 37.08 ($CH_3$—N), 68.38 (CH—OH), 105.79 (CH=C—N), 126.49 (CH—CH=CH—C), 128.12 (CH—CH=CH—C), 128.60 (CH—CH=CH—C), 137.75 (CH=N), 140.88 (CH—CH=CH—C), 144.15 (CH=C—N) ppm.

Example 3

Synthesis of (2-Methyl-2H-pyrazol-3-yl)-phenyl-methanol using 2-aminoethyl diphenylborinate In a 20 ml vial is placed 8.92 mg (10 mol %) of (S)-2-piperidinyl-1,1,2-triphenyl-ethanol and 56 mg of 2-aminoethyl diphenylborinate. The vial is closed and flushed with argon. Dry toluene (2 mL) is added and the vial is placed in a cooling bath of 10° C. Diethylzinc (0.7 mL, 15% in hexane) and 25 µl (0.25 mmol) 2-methyl-2H-pyrazole-3-carbaldehyde is added and the reaction mixture is stirred for at least 12 hours at 10° C. The work-up is conducted as described in Example 2 affording the product alcohol (R)-II (35 mg, 74%) in 89% ee.

Example 4

Influence of the Ligand

Using the optimal conditions [Example 2] which leads to 85–87% ee with the ligand sd499, a ligand screening with a variety of N,O-ligands was carried out. The results are given in the following table.

| ligand (mol %) | | ee (configuration) |
|---|---|---|
| SD499 (5 mol %) | | 84% (R) |
| SD311b (5 mol %) | | 91% (R) |
| TD10a (5 mol %) | | 87% (R) |
| SD498a (5 mol %) | | 78% (R) |
| (S)-2-Piperidinyl-1,1,2-triphenylethanol (5 mol %) | | 87% (R) |
| SD522 (5 mol %) | | 83% (R) |
| SD504 (5 mol %) | | 78% (R) |

| ligand (mol %) | ee (configuration) |
|---|---|
| SD591 (5 mol %) 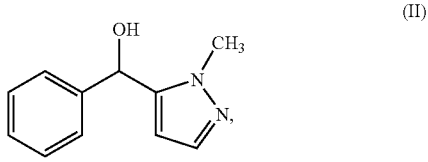 | 85% (R) |
| (S)-2-Piperidinyl-1,1,2-triphenylethanol (10 mol %) | 93% (R) |

The best results were obtained with the ligands sd311b (91% ee) and commercially available (S)-2-piperidinyl-1,1,2-triphenylethanol at 5 mol % scale. As the latter one is known to be a somewhat slower ligand than the paracyclophane-based ligands and the derivatives of sd499, we repeated the experiment with 10 mol % of (S)-2-piperidinyl-1,1,2-triphenylethanol. This experiment gave 93% ee. The ligand is available in both enantiomeric forms.

What is claimed is:

1. A process for the preparation of an enantiomerically enriched compound of formula (II):

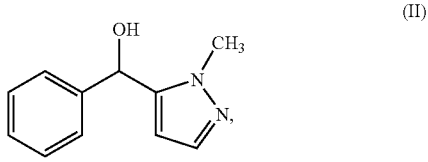

(II)

comprising an enantioselective addition reaction to a pyrazolcarbaldehyde compound of formula (IV):

(IV)

with a phenyl zinc reagent in the presence of a chiral ligand.

2. A process according to claim 1, wherein the phenyl zinc reagent is diphenyl zinc, a mixed zinc species generated from diphenylzinc and diethylzinc, or a diphenyl zinc reagent prepared in situ by a transmetallation reaction of a phenylboron reagent with dimethyl-zinc or diethyl-zinc.

3. A process according to claim 2, wherein the phenylboron reagent comprises a reagent selected from the group consisting of phenylboronic acid, triphenylborane, triphenylborane ammonia complex and 2-aminoethyl diphenylborinate.

4. A process according to claim 1, wherein the chiral ligand is a N,O—, N,N—, N,S—, N,Se— or O,O-ligand in its enantiomerically pure form.

5. A process according to claim 1, wherein the chiral ligand is a N,O-ligand.

6. A process according to claim 5, wherein the O is an alcohol.

7. A process according to claim 5, wherein the N,O-ligand comprises a ligand selected from the group consisting of the following compounds:

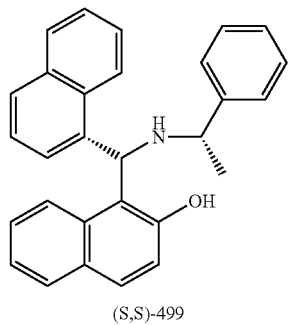

(S,S)-499

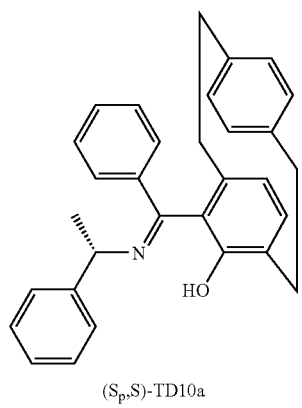

(S$_p$,S)-TD10a

-continued

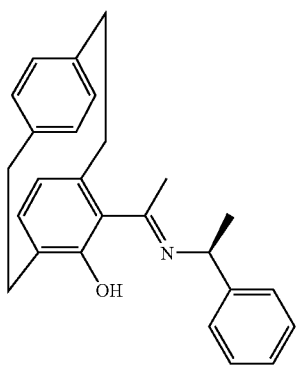

(R_p,S)-311a

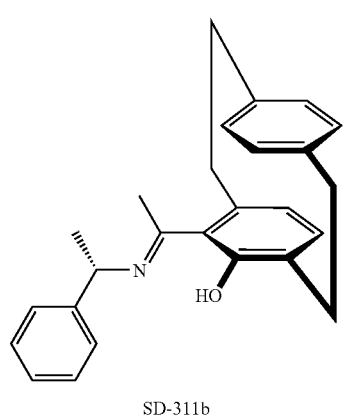

SD-311b

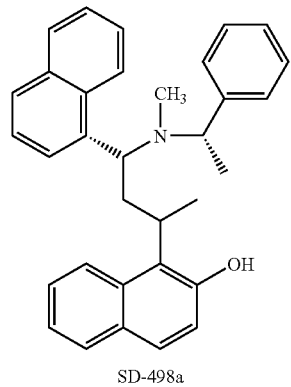

SD-498a

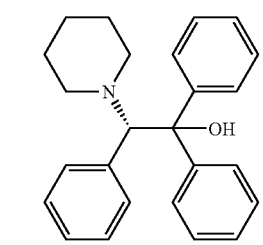

(S)-2-piperidinyl-1,1,2-triphenylethanol

-continued

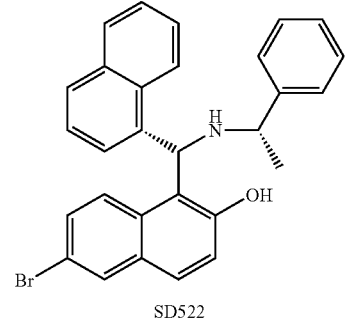

SD522

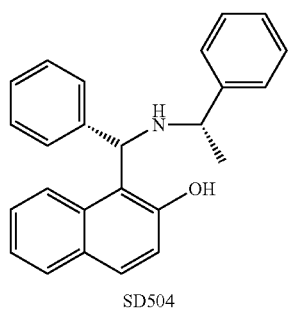

SD504

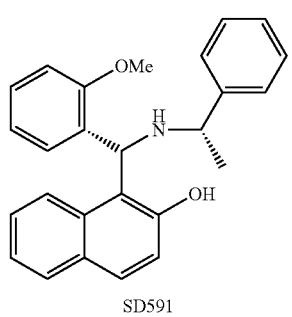

SD591

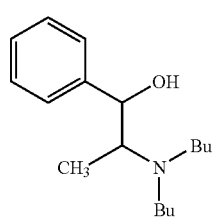

(1R, 2S)-(-)-2-dibuthylamine-1-phenyl-propanol.

8. A process according to claim 1, wherein the ligand is used in an amount in a range of from 1 to 20 mol %.

9. A process according to claim 1, wherein the ligand is used in an amount in a range of from 5 to 10 mol %.

10. A process according to claim 1, wherein the enantioselective addition reaction is conducted at temperature in a range of from 0° C. to 20° C.

11. A process according to claim 1, wherein the pyrazolcarbaldehyde is at a concentration in a range of from 0.01 molar to 2 molar.

12. A process according to claim 1, wherein the enantioselective addition reaction is conducted in solvent medium.

13. A process according to claim 12, wherein the solvent medium comprises toluene or hexane.

14. A process according to claim 1, which further comprises an O-alkylation of the enantiomerically enriched compound of formula II to prepare respectively (+)-Cizolirtine (+)-2-[phenyl(1-methyl-1H-pyrazol-5-yl)methoxy]-N,N-dimethylethanamine and (−)-Cizolirtine (−)-2-[phenyl(1-methyl-1H-pyrazol-5-yl)methoxy]-N,N-dimethylethanamine.

15. A process according to claim 14, wherein the O-alkylation is carried out, without an intermediate separation or purification step.

16. A process for the preparation of a precursor alcohol of Cizolirtine, (±)-2-[phenyl(1-methyl-1H-pyrazol-5-yl)methoxy]-N,N-dimethylethanamine and its enantiomers, comprising asymmetric addition of a metalated phenyl reagent to a pyrazolcarbaldehyde in the presence of a chiral ligand to yield said precursor alcohol.

17. A process for the preparation of Cizolirtine (±)-2-[phenyl(1-methyl-1H-pyrazol-5-yl)methoxy]-N,N-dimethylethanamine or its enantiomers, comprising asymmetric addition of a metalated phenyl reagent to a pyrazolcarbaldehyde in the presence of a chiral ligand to yield chiral alcohols, and O-alkylating said chiral alcohols to yield Cizolirtine (±)-2-[phenyl(1-methyl-1H-pyrazol-5-yl)methoxy]-N,N-dimethylethanamine or its enantiomers.

18. A process according to claim 17, wherein said O-alkylating is conducted with an intermediate separation or purification step.

* * * * *

UNITED STATES PATENT AND TRADEMARK OFFICE
CERTIFICATE OF CORRECTION

PATENT NO. : 7,109,349 B2
APPLICATION NO. : 11/041637
DATED : September 19, 2006
INVENTOR(S) : Antoni Torrens Jover et al.

It is certified that error appears in the above-identified patent and that said Letters Patent is hereby corrected as shown below:

On Title Page Item (30)
"Dec. 7, 2004   (EP) ............................ 04380266" should be
-- Dec. 17, 2004      (EP) ............................ 04380266.9 --.

At column 3, line 26, "nitrites" should be -- nitriles --.

At column 6, in structure type (V) illustrated at lines 8-17, "$R^1$" should be -- R' --

Signed and Sealed this

Nineteenth Day of December, 2006

JON W. DUDAS
*Director of the United States Patent and Trademark Office*